United States Patent
Zeng et al.

(10) Patent No.: US 9,682,121 B2
(45) Date of Patent: Jun. 20, 2017

(54) APPLICATION OF IRISIN IN MYOCARDIAL ISCHEMIA REPERFUSION

(71) Applicant: THIRD AFFILIATED HOSPITAL, THIRD MILITARY MEDICAL UNIVERSITY, Chongqing (CN)

(72) Inventors: Chunyu Zeng, Chongqing (CN); Yu Han, Chongqing (CN); Zhen Wang, Chongqing (CN); Ken Chen, Chongqing (CN); Yu Li, Chongqing (CN)

(73) Assignee: THIRD AFFILIATED HOSPITAL, THIRD MILITARY MEDICAL UNIVERSITY, Chongqing (CN)

( * ) Notice: Subject to any disclaimer, the term of this patent is extended or adjusted under 35 U.S.C. 154(b) by 0 days.

(21) Appl. No.: 15/035,646

(22) PCT Filed: Jun. 27, 2014

(86) PCT No.: PCT/CN2014/080938
§ 371 (c)(1),
(2) Date: May 10, 2016

(87) PCT Pub. No.: WO2015/070619
PCT Pub. Date: May 21, 2015

(65) Prior Publication Data
US 2016/0296598 A1 Oct. 13, 2016

(30) Foreign Application Priority Data
Nov. 16, 2013 (CN) .......................... 2013-10572068

(51) Int. Cl.
*A61P 9/10* (2006.01)
*A61K 38/22* (2006.01)
*A61K 38/17* (2006.01)
*A61K 35/30* (2015.01)
*C07K 14/575* (2006.01)

(52) U.S. Cl.
CPC .......... *A61K 38/1709* (2013.01); *A61K 35/30* (2013.01); *A61K 38/22* (2013.01); *C07K 14/575* (2013.01)

(58) Field of Classification Search
None
See application file for complete search history.

(56) References Cited

FOREIGN PATENT DOCUMENTS

CN 103585620 A 2/2014
WO 02092111 A1 11/2002

OTHER PUBLICATIONS

The World Intellectual Property Organization (WIPO) International Search Report for PCT/CN2014/080938 Oct. 10, 2014.
Lecker, S.H. et al., "Expression of the Irisin Precursor FNDC5 in Skeletal Muscle Correlates With Aerobic Exercise Performance in Patents with Heart Failure", Circulation Heart Failure, vol. 5, Sep. 20, 2012 (Sep. 20, 2012), ISSN: pp. 812-828, See the whole document.
Yang, Yeyi et al., "Research process of Myocardial Ischemia Reperfusion Injury Preservation Agent", Practical Preventive Medicine, No. 02, vol. 15, Apr. 30, 2008 (Apr. 30, 2008), ISSN: pp. 616-618, see the whole document.

*Primary Examiner* — Zachary Howard
(74) *Attorney, Agent, or Firm* — Anova Law Group, PLLC (57) ABSTRACT

The invention discloses application of irisin in the preparation of drugs for preventing myocardial ischemia reperfusion injuries. Experimental results show that irisin can decrease the myocardial infarction area caused by ischemia reperfusion, reduce the increase of the contents of lactate dehydrogenase (LDH), troponin (cTnI), creatine kinase (CK), and other myocardial enzyme markers caused by ischemia reperfusion, meanwhile reducing the inflammatory response, myocardial apoptosis, and oxidative stress response caused by myocardial ischemia reperfusion, promote peroxysome proliferator-activated receptor γ nuclear translocation, and inhibit nuclear transcription factor NF-κB nuclear translocation and accordingly decrease myocardial structure injuries and load increase caused by ischemia reperfusion. Therefore, irisin can be used for preventing and decreasing myocardial reperfusion injuries and has important clinical significance on the treatment of myocardial ischemia.

13 Claims, 9 Drawing Sheets

APPLICATION OF IRISIN IN MYOCARDIAL ISCHEMIA REPERFUSION

CROSS-REFERENCES TO RELATED APPLICATIONS

This application is a national phase entry under 35 U.S.C. §371 of International Application No. PCT/CN2014/080938, filed on Jun. 27, 2014, which claims the priority of Chinese patent application Serial No. 201310572068.2 filed with the State Intellectual Property Office of P. R. China on Nov. 16, 2013, the entire contents of both of which are incorporated herein by reference.

BACKGROUND OF THE INVENTION

1. Technical Field

The invention belongs to the field of medicine and particularly relates to the application of irisin in the preparation of drugs for preventing myocardial ischemia reperfusion injuries.

2. Description of Related Art

Ischemic heart disease is one of the main diseases leading mortality in the world and greatly threatens human health. The pathology of ischemic cardiomyopathy is shown as that due to blood vessel blockages caused by coronary atherosclerosis or thrombosis, blood circulation is suffocated or interrupted which unbalances the myocardial oxygen and energy supply and disrupts the myocardial energy metabolism, and histopathological damage is caused, such as myocardial infarctions and heart failure. At present, the most effective treatment method for overcoming ischemia is blood vessel re-dredging for blood supply restoration, including balloon dilatation, arteriovenous thrombolysis, extracorporeal circulation, coronary artery bypass surgery and the like, namely reperfusion. However, after myocardial ischemia reperfusion injuries were put forward in 1960 for the first time, medical workers have been plagued by this problem, a large number of animal experiments and clinical results show that although reperfusion greatly improves the myocardial blood supply, instead further worsening of the tissue damage caused during ischemia is seen due to the fact that a large amount of oxygen-rich blood and other nutrients flows into the ischemic area, and arrhythmia, cardiac rupture, heart failure and other complications are caused. Clinical studies show that myocardial ischemia reperfusion injuries are very common in cardiovascular surgery and account for a large proportion of early death caused by coronary artery bypass surgery, myocardial infarction, heart transplantation failure and so on and so forth. Therefore, how to prevent and abate myocardial reperfusion injuries has become a significant clinical topic.

The specific mechanism of myocardial ischemia reperfusion injuries remains unclear. Myocardial ischemia causes insufficient energy metabolism and ATP depletion, intracellular calcium overload occurs in the reperfusion process producing a large number of oxygen free radicals, and membrane phospholipids, proteins, and DNA are directly or indirectly damaged. Meanwhile, chemotaxis and infiltration of neutrophile granulocytes and other inflammatory cells and production and secretion of inflammatory factors also play an important role in myocardial reperfusion injuries. These inflammatory responses not only directly damage myocardial tissues, but also immune vascular injuries are caused. Yet, the clinical application effect of preventing and treating myocardial reperfusion injuries by removing free oxygen (superoxide dismutase, reduced glutathione, etc.), improving the metabolism of ischemic tissues (e.g., creatine phosphate and trimetazidine), adding immune inhibitors and the like is not good. Therefore, an effective treatment method or medicament having a small side effect and used for prevention and treatment of myocardial ischemia reperfusion injuries is urgently needed.

A peroxide proliferator-activated receptor synergy promoter (PGC-1α) is a transcriptional co-activation factor and mediates a lot of energy metabolism related biological processes, especially in the aspect of the regulation of mitochondrial biosynthesis and oxidative metabolism conducted on various cells. In 2012, Boström found that PGC-1α expressions of skeletal muscles can be promoted through exercise, and while PGC-1α enables the level of fibronectin III-type domain containing proteins 5 (FNDC5) to rise, FNDC5 is a transmembrane protein with a total length of 196 amino acids of the fibronectin III-type domain containing proteins, and is a powerful inducer for inducing brown fat formation, the hydrolysis fragments thereof can be secreted into the blood to be circulated in the blood, and the FNDC5 content in myocardiums is very high, its functional effect on the heart is unclear at present, and clinical studies show that the FNDC5 expression in patients with heart failure is decreased somewhat. After an N-terminal signal peptide is removed from FNDC5, the FNDC5 cracks at the GLU142 position to form a polypeptide of about 110 amino acids, and the polypeptide is named irisin. At present, it is still unknown whether irisin has an effect on myocardial ischemia reperfusion injuries or not.

BRIEF SUMMARY OF THE INVENTION

In view of this, one of the purposes of the invention is to provide application of irisin in the preparation of drugs for preventing myocardial ischemia reperfusion injuries.

For achieving the purposes of the invention, the technical scheme is as follows:

Application of irisin in the preparation of drugs for preventing myocardial ischemia reperfusion injuries, wherein the amino acid sequence of irisin is shown in the description of SEQ ID NO.1:

Asp Ser Pro Ser Ala Pro Val Asn Val Thr Val Thr Val Arg His Leu Lys Ala Asn Ser Ala Val Ser Trp Asp Val Leu Glu Asp Glu Val Ile Gly Phe Ala Ile Ser Gln Lys Asp Val Arg Met Leu Arg Phe Ile Gln Glu Val Asn Thr Arg Ser Cys Ala Leu Trp Asp Leu Glu Asp Thr Glu Tyr Ile Val His Val Glu Ala Ile Ser Ile Gln Gly Glu Ser Pro Ala Ser Glu Pro Val Leu Phe Lys Thr Pro Arg Glu Ala Glu Lys Met Ala Ser Lys Asn Lys Asp Glu Val Thr Met Lys Glu

Further, the application of irisin in the preparation of drugs for preventing myocardial infarction caused by myocardial ischemia reperfusion.

Further, the application for irisin in the preparation of drugs for preventing myocardial enzyme marker rise caused by myocardial ischemia reperfusion; even further, the myocardial enzyme marker is lactic dehydrogenase, troponin or creatine kinase.

Further, the application of irisin in the preparation of drugs for preventing inflammatory response caused by myocardial ischemia reperfusion.

Further, the application of irisin in the preparation of drugs for preventing oxidative stress caused by myocardial ischemia reperfusion.

Further, the application of irisin in the preparation of drugs for preventing myocardial apoptosis caused by myocardial ischemia reperfusion.

Further, the application of irisin in the preparation of drugs for promoting peroxysome proliferator-activated receptor γ nuclear translocation.

Further, the application of irisin in the preparation of drugs for inhibiting nuclear transcription factor NF-κB nuclear translocation.

The invention has the advantages that the invention discloses the application of irisin in the preparation of drugs for preventing myocardial ischemia reperfusion injuries, the effect of irisin on cardiac dysfunction caused by ischemia reperfusion is studied by establishing an SD rat myocardial ischemia reperfusion model, an experiment proves that the exogenous irisin can obviously decrease the enlargement of the myocardial infarction area and myocardial zymogram marker (cTnI, LDH and CK) release caused by ischemia reperfusion and inhibit the decline and contraction of the left ventricular ejection fraction and end-diastolic volume rise caused by ischemia reperfusion; therefore, irisin can attenuate myocardial structural injuries and load increase caused by ischemia reperfusion; in addition, irisin significantly reduces myocardial apoptosis, inflammatory factor synthesis and release, inflammatory cellular infiltration and oxidative stress caused by ischemia reperfusion, and the effect of resisting myocardial ischemia reperfusion injuries of irisin is further proved. The present invention also simulates in-vivo myocardial ischemia reperfusion through an in-vitro H9C2 myocardial cell experiment (including hypoxia/reoxygenation and $H_2O_2$ treatment) to explore the effect and influence of irisin on myocardial cell hypoxia/reoxygenation injuries, wherein an in-vitro experiment result is similar to an in-vivo experiment result, namely that exogenous irisin effectively inhibits myocardial cell viability drops caused by hypoxia/reoxygenation and reduces myocardial cell LDH release caused by hypoxia/reoxygenation, and a dose-dependent relationship is shown. An immunofluorescence experiment shows that irisin involved in myocardial cell endochylema is increased when myocardial cell hypoxia/reoxygenation occurs, and the DNA agglutination phenomenon of the myocardial cells is significantly diminished after excessive exogenous irisin is added; the effect of irisin on the myocardial cells subjected to $H_2O_2$ treatment is similar to that of the former. These results prove that irisin indeed has the effect of resisting myocardial cell hypoxia/reoxygenation injuries.

The invention further provides research on a part of the signal mechanism of irisin resistant to ischemia reperfusion injuries, and a result shows that in the myocardial cells undergoing ischemia reperfusion, irisin promotes PPARγ translocation from endochylema to nuclei so as to inhibit NF-κB translocation from endochylema to nuclei and accordingly proves that irisin plays a resisting role against myocardial cell injuries partly through PPARγ. In addition, a study on how to influence PPARγ translocation in myocardial cells with irisin is also made, the myocardial cell injury resisting effect of irisin obviously declines when excessive Nystatin is added, and irisin may enter the cells partly through lipid rafts to regulate PPARγ and NF-κB so as to play the role. Because the main constituent component of the lipid rafts is caveolin 1, which is an important scaffolding protein, irisin may cause caveolin 1 to increase and may promote PPARγ nuclear translocation and inhibit NF-κB nuclear translocation partly through caveolin 1 and thus play a protective role.

According to the invention, it is found that irisin can be used for the prevention and treatment of myocardial ischemia reperfusion injuries (the myocardial infarction area is enlarged, released myocardial markers are increased, cardiac load is increased, and inflammatory response, oxidative stress, and apoptosis are increased) for the first time, and the inhibiting of inflammatory responses can be explained by the following mechanism: NF-κB-related inflammatory factor expression is inhibited, the tissue infiltration of inflammatory cells is reduced and the inflammatory response after reperfusion is obviously reduced by promoting PPARs translocation towards the nuclei. The invention puts forward and proves that irisin has the effect of resisting ischemia reperfusion injuries of tissues and organs for the first time, and not only is the research and application range of irisin widened, but a new target and field of view for the prevention and treatment of ischemia reperfusion injuries is provided. Due the fact that irisin is a secreted protein of the human body and the side effects brought by irisin are relatively small, irisin can be used in medicines and health-care products.

BRIEF DESCRIPTION OF THE SEVERAL VIEWS OF THE DRAWINGS

The further features of the invention are more comprehensively described with the following drawings.

DETAILED DESCRIPTION OF THE INVENTION

The embodiment of the invention is preferably described in detail, as being combined with the following drawings. Common experimental methods are not indicated in the embodiments, and performed by the guidance of *Molecular Cloning: The Laboratory Manual* (third edition, written by J. Sam Brooker et al), or the manufacturers of experimental device.

The SD rats, weighting of 250 to 260 g, used in experiment are obtained from the Experimental Animals Centre of Daping Hospital, the Third Military Medical University at Chongqing, China. All experiments were conformed to the guidelines of the American Association for the Accreditation of Laboratory Animal Care.

The data are analyzed by SPSS Statistics 12.0 software (IBM, Chicago). and expressed as mean±SEM. Comparison within groups was made by ANOVA. A value of $P<0.05$ was considered significant.

I. Irisin improves ischemia reperfusion induced cardiac dysfunction

The SD rats are randomly divided into five groups: the sham-operated group, heart ischemia reperfusion (IR) group, heart ischemia reperfusion+irisin (IR+Irisin) group, heart ischemia reperfusion+antibody pre-adsorbed irisin (IR+Irisin/Ab, 1:5 w/w incubation) group and heart ischemia reperfusion+heat-inactivated irisin group (IR+Irisin (HI)). Irisin is administrated 30 min before ischemia or after ischemia immediately. The dosage of irisin in each group is 5 μg/kg. The rats are anesthetized with an intraperitoneal injection of sodium pentobarbital (50 mg/kg) 30 min after irisin administration and placed on a heating pad to maintain their body temperature (37° C.). After thoracotomy of left thorax, the left anterior descending branch of coronary artery is ligated for 30 minutes and released for 24 hours-reperfusion process. After reperfusion, the blood samples and myocardial tissues are obtained for myocardial zymogram analysis and infarct size measurement to determine the protective effect of irisin on ischemia reperfusion induced cardiac dysfunction.

Figure 1:
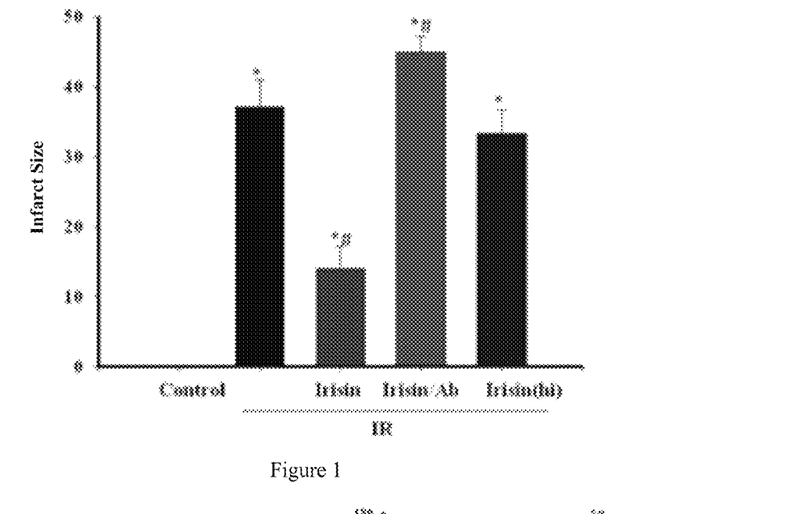
FIG. 1 shows the data of infarct size after myocardial ischemia reperfusion injury by TTC staining (* represents a comparison with a control group, # represents a comparison with an I/R group, $P<0.05$, $n=12$)

Infarct size measurement: Hearts from rats cleared of blood with saline is infused with 1% Evens blue via aortic orifice after ligating the left anterior descending branch, and sectioned transversely into 5 pieces, incubated in 1% TTC solution at 37° C. for 15 minutes. The myocardial infarct size is determined by Image J software (NIH), and the results are shown in FIG. 1. As shown in FIG. 1, the infarction size of the IR+Irisin group is significantly smaller than those of other operated groups, which indicated that irisin might decrease heart ischemia reperfusion injuries.

Figure 2:
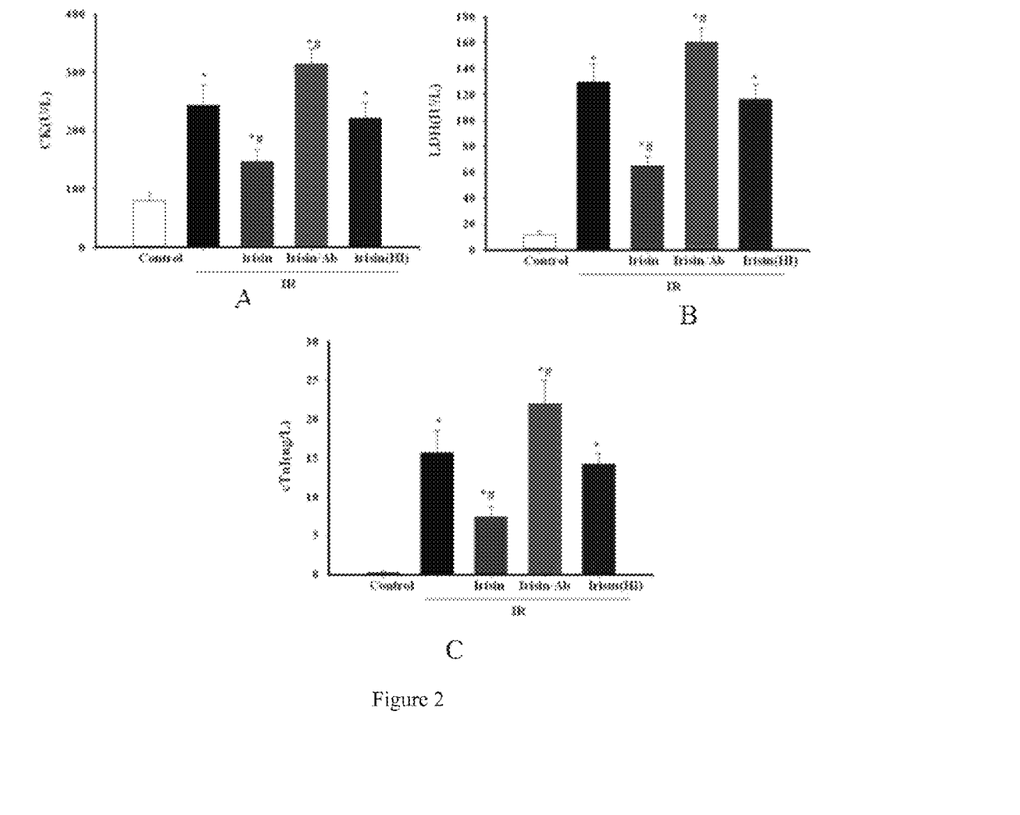
FIG. 2 shows the myocardial zymogram after myocardial ischemia reperfusion (A: cTnI expression; B: LDH expression; C: CK expression, * represents a comparison with the control group, # represents a comparison with the I/R group, $P<0.05$, $n=12$)

Myocardial zymogram analysis: The blood samples from SD rats is collected and centrifuged at 3,000 g for 10 minutes to obtain serum. The level of lactic dehydrogenase (LDH), troponin (cTnI) and creatine kinase (CK) are detected respectively by Beckman Coulter AU clinical biochemical kits or other assay kits under the guidance of user manual. The data are shown in FIG. 2. Compared with the sham-operated group, the LDH, cTnI and CK level of the IR group are significantly increased, which are decreased by irisin administration. The protective effect of irisin is blocked when irisin is pre-adsorbed with antibody or inactivated by heat.

Figure 3:
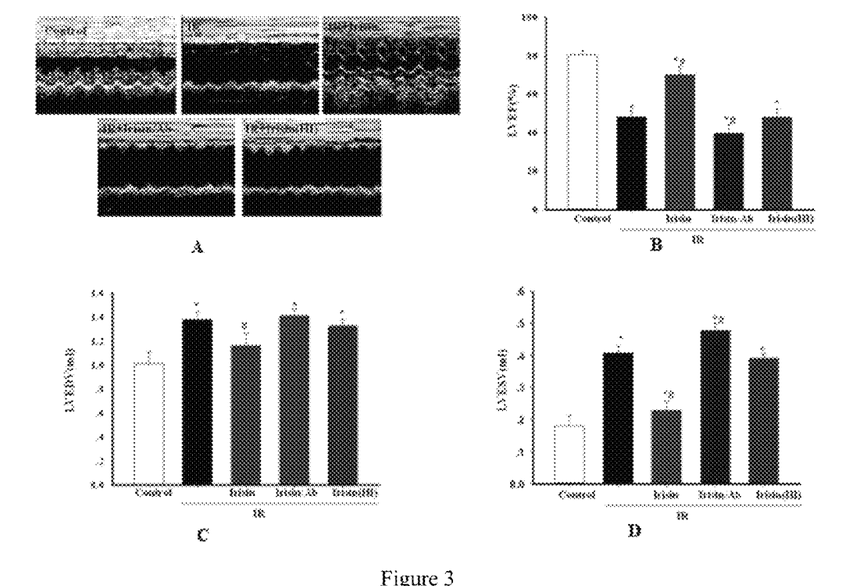
FIG. 3 shows the effect of irisin on myocardial ischemia reperfusion (A: echocardiogram; B: left ventricular ejection fraction; C: left ventricular end-diastolic volume; D: left ventricular end-systolic volume; * represents a comparison with the control group, # represents a comparison with the I/R group, $P<0.05$, $n=12$)

Echocardiography for assessment of heart function: SD rats are anesthetized and placed on operation plate. Left ventricular ejection fraction (LVEF), Left ventricular end-diastolic volume (LVEDV), and Left ventricular end-systolic volume (LVESV) are measured and analyzed in the left ventricular long-axis view by a 760 MHz ultrasonic transducer. The detection of each rat is repeated 3 times. The data of each rat is expressed as average and standard deviation. As shown in FIG. 3, The LVEF of I/R rats is reduced while the LVEDV and the LVESV are increased. Irisin administration reverses the negative changes. The protective effect of irisin is blocked when irisin is pre-adsorbed with antibody or inactivated by heat. Thus, the data indicate that an appropriate concentration of irisin can effectively improve the ischemia reperfusion induced cardiac dysfunction via the functional components of irisin, rather than the structural components.

Figure 4:
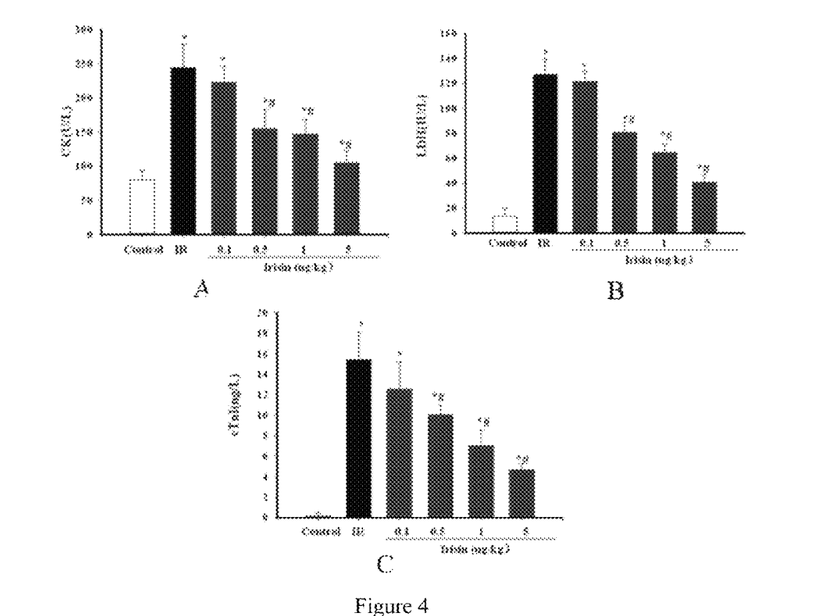
FIG. 4 shows the effect of irisin of different concentrations on myocardial zymogram expression after myocardial ischemia reperfusion (A: cTnI expression; B: LDH expression; C: CK expression, * represents a comparison with the control group, # represents a comparison with the I/R group, $P<0.05$, $n=12$)

As the same methods describing above, different doses of irisin (0.1 μg/kg, 0.5 μg/kg, 1 μg/kg and 5 μg/kg) are treated to heart ischemia reperfusion injured rats. The level of LDH, cTnI and CK are determined. As shown in FIG. 4, the level of LDH, cTnI and CK could be reduced by irisin treatment in a dose-dependent manner. Irisin shows a positive effect to heart injury, and the peak elevation of protective effect is observed at the concentration of 5 μg/kg.

Figure 5:
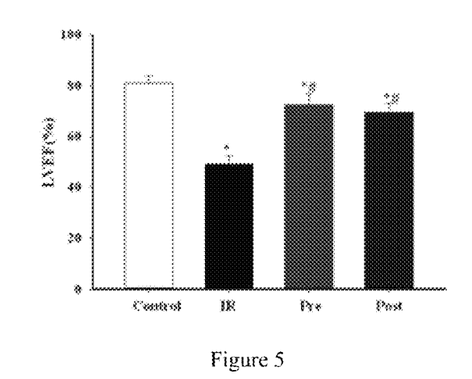
FIG. 5 shows the data of left ventricular ejection fraction.
Figure 6:
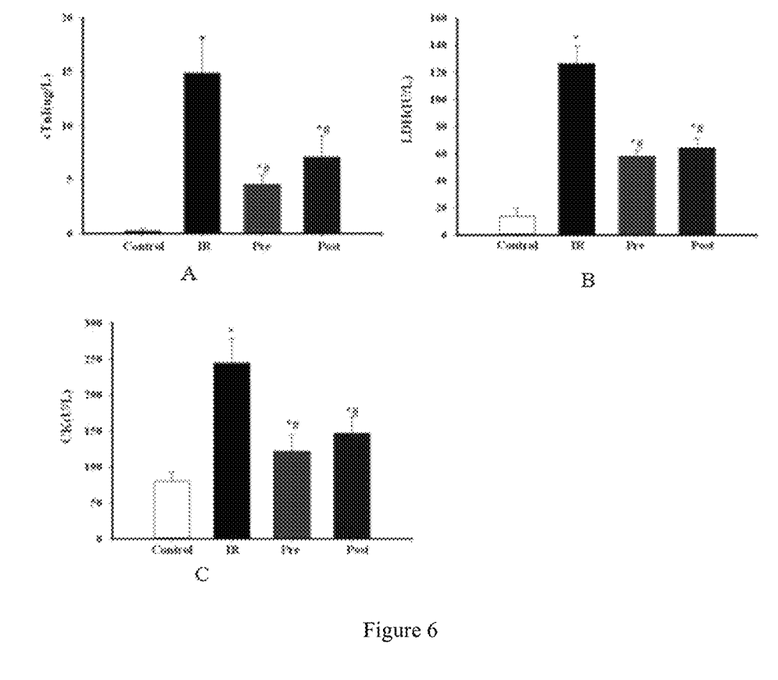
FIG. 6 shows the precondition (30 minutes before ischemia) and treatment (after ischemia immediately) effect of irisin on myocardial ischemia reperfusion injuries (A: cTnI expression; B: LDH expression; C: CK expression, * represents a comparison with the control group, # represents a comparison with the I/R group, $P<0.05$, $n=13$)

Heart ischemia reperfusion model is performed, as previously described. Irisin (5 μg/kg) is administrated 30 minutes before ischemia (pre) or after ischemia immediately (post). The left ventricular ejection fraction and myocardial zymogram are measured. The data are shown in FIG. 5, and FIG. 6. Irisin administration 30 minutes before ischemia or after ischemia immediately reverses the decreasing LVEF, and significantly reduced LDH, cTnI and CK. The effect of irisin administration before ischemia is better. The data indicates that irisin could be used for prevent or treat the ischemia reperfusion injuries.

Figure 7:
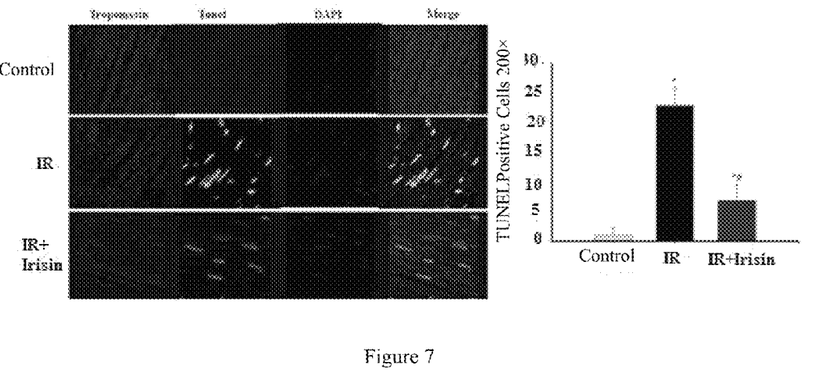
FIG. 7 shows the result of myocardial apoptosis by TUNEL staining.

II. Irisin reduces heart ischemia reperfusion induced inflammatory response, oxidative stress and apoptosis TUNEL staining for assessment of myocardial cell apoptosis: The myocardial cell apoptosis detection is performed by TUNEL staining kit. Heart tissues from each group cleared of blood with saline and keep in 4% neutral-buffered paraformaldehyde for 1-2 days at 4° C., are sectioned (4 μm), embedded in paraffin, and mounted on slides. The tissue is deparaffinized and rehydrated by successive incubations in xylene, 100% ethanol, 95% ethanol, 75% ethanol, and phosphate buffer saline (PBS), incubated in a solution containing 20 μg/mL protein kinase K at 37° C. for 60 minutes and then incubated in 1% trinitrotoluene X-100 for 8 minutes. After washing with PBS twice, the slices are incubated with 50 μL of TUNEL reaction mixture at 37° C. for 60 minutes and kept in dark. After staining nuclei with DAPI, the images were acquired by fluorescence microscopy in a 200× view field. As shown in FIG. 7, compared with the control group, the number of TUNEL positive cells detected of the IR group remarkably rises but declines very obviously after irisin is used, and it is indicated that irisin has the effect of inhibiting apoptosis.

Figure 8:
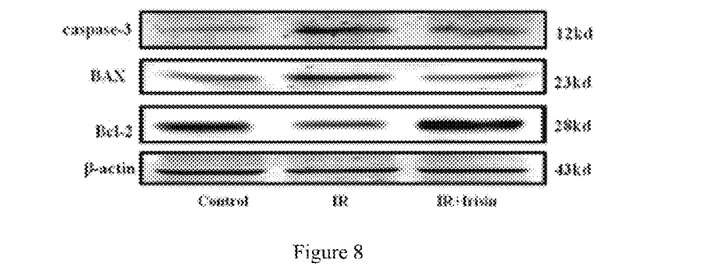
FIG. 8 shows the expression of apoptosis related protein (Bcl-2, Bax and caspase-3)

Bcl-2, Bax, and caspase-3 protein expression is detected by immunoblotting. The heart tissue of infarct zone from sham-operated group, IR group and IR+irisin group are homogenized for polyacrylamide gel electrophoresis (50 µg). The amount of protein are transferred onto the PVDF membranes and blocked by TBS containing 5% (volume percentage) fat-free milk for 1 hour. The transblots were probed with the Bcl-2 antibody (1:500), Bax antibody (1:500), caspase-3 antibody (1:500) and β actin antibody (1:1000) at 4° C. overnight. After washing with TBS three times, membranes are incubated with goat anti-rabbit IgG (1:10,000) at room temperature for 1 hour. As shown in FIG. 8, compared with the control group, the expression of caspase-3 and Bax of the IR group significantly rise while the expression of Bcl-2 declines. Irisin decreases the caspase-3 and Bax expression and increases the Bcl-2 expression, which indicate that irisin has the protective effect on apoptosis.

Figure 9:
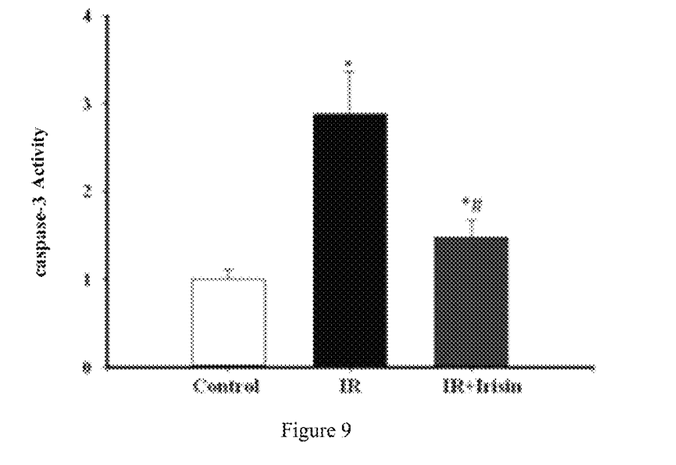
FIG. 9 shows the activity of caspase-3.

Caspase-3 activity is detected as follow: tissues are homogenized with lysate (10 µl/µg tissue) on the ice bath. After clarification of the lysates by centrifugation at 12,000 g for 15 min, the supernatants were collected and the protein concentrations were determined using a Bradford protein assay kit. Lysates and Ac-DEVD-pNA (2 mM) are added into the sample to be determined to perform incubation at the temperature of 37° C. for 60 minutes; the buffer solution to be determined and the Ac-DEVD-pNA (2 mM) are added into a blank control, and absorbance can be determined under the condition of 405 nm when a relatively obvious color change is found. $A_{405}$ of the blank control is removed from $A_{405}$ of the sample, namely absorbance produced by the pNA generated through caspase-3 catalysis in the sample, and the calculation results as shown in FIG. 9. As shown in FIG. 9, compared with the control group, the caspase-3 activity of the IR group remarkably rises but is obviously reduced after irisin is used, and the results indicate that irisin has the obvious effect of inhibiting apoptosis.

The markers of oxidative stress such as myeloperoxidase (MPO), malondialdehyde (MDA) and superoxide dismutase (SOD) after ischemia reperfusion are detected by ELISA. Heart tissues from SD rats of sham-operated group, IR group and IR+irisin groupare homogenized in ice-cold lysis buffer, centrifuged at 16,000 g for 10 minutes at 4° C. The supernatants is collected for the measurement of MPO, MDA and SOD level (the detection kit is provided by Shanghai Biyuntian biotechnology CO., LTD.). Tissue samples are prepared according to the steps, the ELISA kit of R&D Systems Company is adopted to detect the contents of inflammatory factors in plasma and the myocardial tissues, the detection results of the inflammatory factors in the plasma are shown in FIG. 11, and the detection results of the inflammatory factors in the myocardial tissues are shown in FIG. 12.

Figure 10:
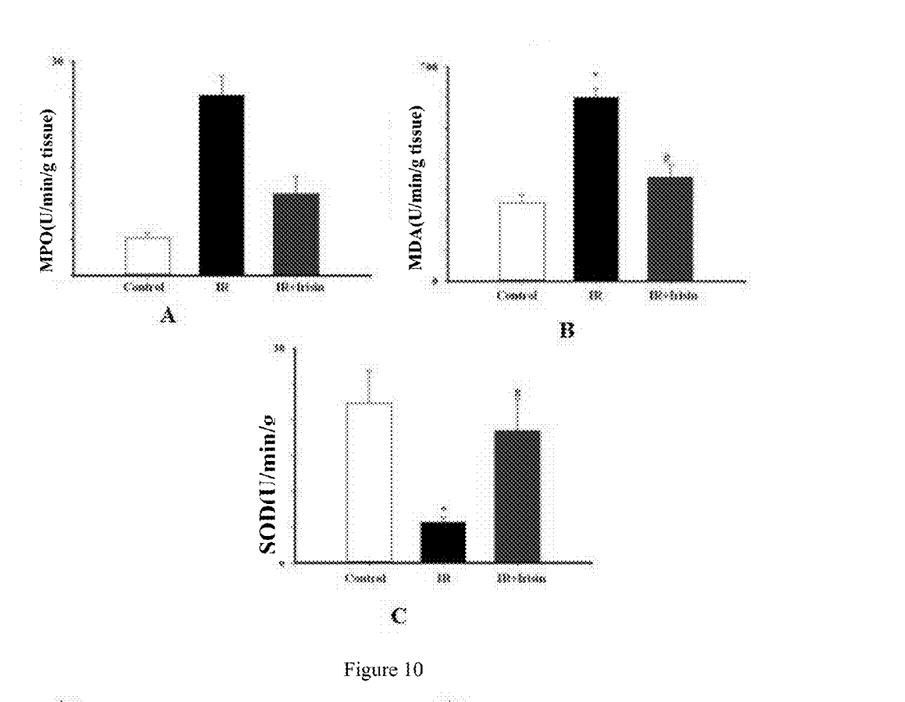
FIG. 10 shows the measurement of oxidative stress after ischemia reperfusion (A: MPO concentration; B: MDA concentration; C: SOD concentration)
Figure 11:
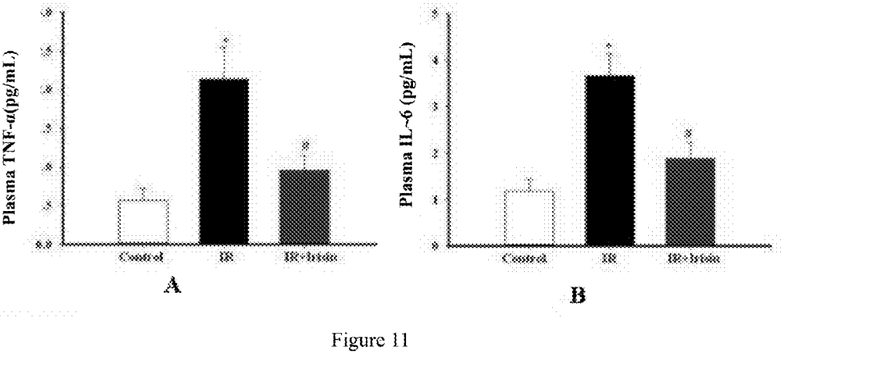
FIG. 11 shows the concentration of an inflammatory factor in plasma (A: TNF-α concentration; B: IL-6 concentration)
Figure 12:
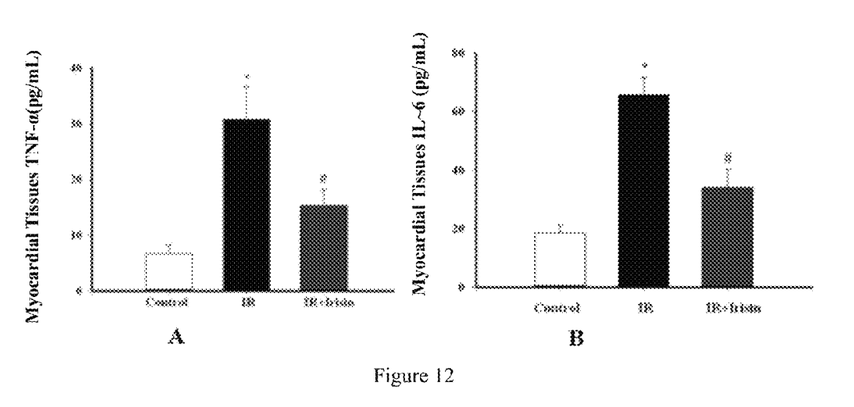
FIG. 12 shows the concentration of inflammatory factor in myocardial tissue (A: TNF-α concentration; B: IL-6 concentration)

As shown in FIGS. 10-12, with respect to the data of MPO, IL-6 and TNF-α level, the inflammatory factor level of the IR group is obviously much higher than that of the sham-operated group, the levels of oxidative stress markers and the inflammatory factors are effectively reduced after irisin treatment, and the effect on inhibiting the inflammatory and oxidative stress response of irisin are reflected. The MDA measurement result is similar to the former while the level of the IR group decreases obviously in the SOD measurement result, but the level greatly rises after irisin is used. Similarly, these results indicate that irisin can obviously inhibit inflammatory response and oxidative stress response caused by reperfusion.

III. The protective effect of irisin on hypoxia/reoxygenation and $H_2O_2$ induced myocardial cell injuries.

Figure 13:
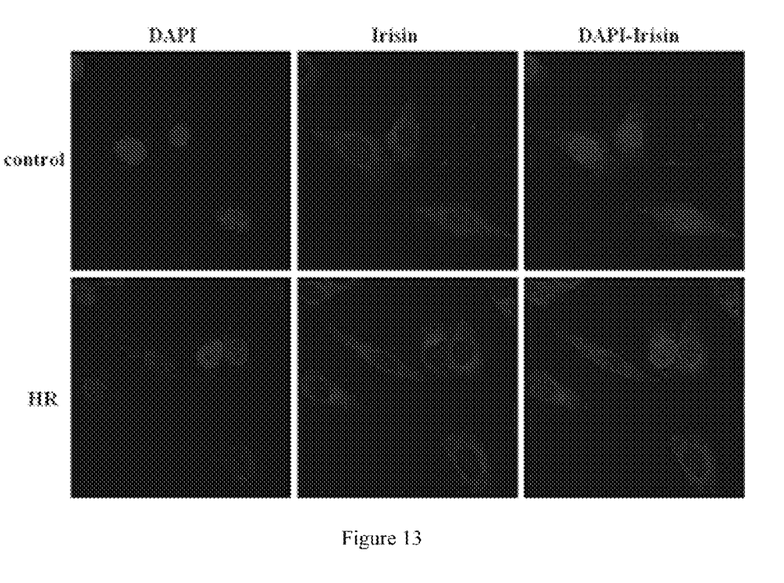
FIG. 13 shows the effect of irisin on H9C2 myocardial cell after hypoxia/reoxygenation, determined by immunofluorescence staining.

H9C2 myocardial cells are cultured in DMEM solution containing high-temperature inactivated FBS of 10% volume, 100 U/mL of penicillin G, 100 mg/mL of streptomycin and 2 mM of L-glutamine. The cultured cells are divided into 3 groups: group I: control group, group II: HR group ($N_2$ perfusion), and group III: HR+irisin group (Cells are treated with different concentrations of irisin 30 minutes before $N_2$ perfusion). An H9C2 myocardial cell culture plate is arranged in anoxic chamber with two holes for gas perfusion and discharge. Cells were exposed to an anoxic chamber with 5% $CO_2$ and 95% $N_2$ at 37° C. for 16 h followed by reoxygenation for up to 3 h After that, the localization of irisin in hypoxia/reoxygenation treated H9C2 myocardial cells is determined by immunofluorescence staining, and the results are shown in FIG. 13. As shown in FIG. 13, chromatin agglutination of the hypoxia/reoxygenation myocardial cells is obviously stronger, more irisin gather towards the endochylema, and this phenomenon indicates that irisin is possibly involved in cell repair during myocardial cell hypoxia/reoxygenation and also explains the phenomenon that irisin content in the blood will drop after myocardial ischemia reperfusion.

Figure 14:
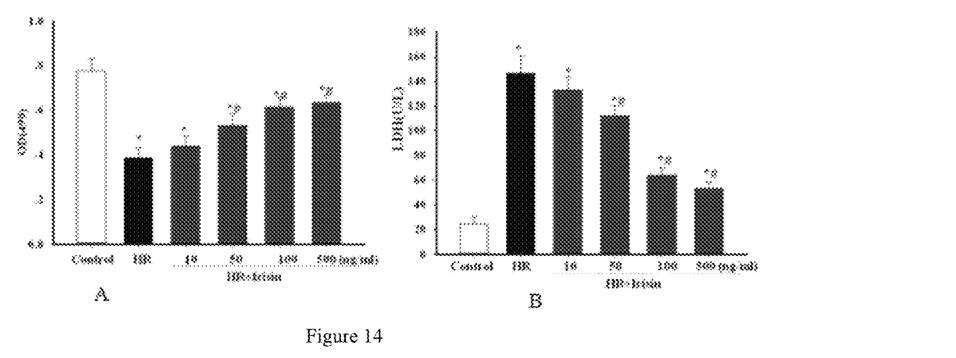
FIG. 14 shows the cell viability and LDH concentration in H9C2 myocardial cells after hypoxia/reoxygenation with or without irisin (A: cell viability; B: LDH concentration)

The cell viability is determined by MTT assay. The specific method comprises the steps of removing the supernatant of the mixed cell liquid, washing the cells with a PBS solution 3 times, adding 200 µL of a 5% thiazole blue solution train into the chambers formed in the cell culture plates to perform a culture for 4 hours, carefully removing the culture solution in the holes after the culture is completed, then adding 150 µL of DMSO solution respectively, carrying out slight oscillation for 10 minutes, and finally using a microplate reader to conduct optical density value detection on the holes in the plates at the position of 490 nm wavelength, and the result is shown in FIG. 14A. At the same time, the kit is utilized to measure the LDH content, and the result is shown in FIG. 14B. The results show that when the myocardial cells are cultured under normal conditions, irisin has no obvious influence on the cell viability. In the case of hypoxia/reoxygenation, it can be seen that the OD value is decreased obviously but can be recovered to some degree after irisin is used, and the effect and irisin present a dose-dependent relationship. After the irisin dose is more than 500 ng/mL, the effect of irisin is best, the OD value is approximately proportional to the cell vitality, and therefore it is indicated that irisin can enhance the vitality of the myocardial cells to resist cell vitality reduction caused by hypoxia/reoxygenation. Due to the fact that the intracellular LDH is released to the outside during hypoxia/reoxygenation, the LDH concentration rises; from FIG. 14B, it can be seen that the LDH concentration of the HR group is much higher than that of the control group, but is reduced after use of irisin, the dose-dependent relationship is presented, and the effect is most obvious when the irisin dose is 500 ng/mL.

Figure 15:
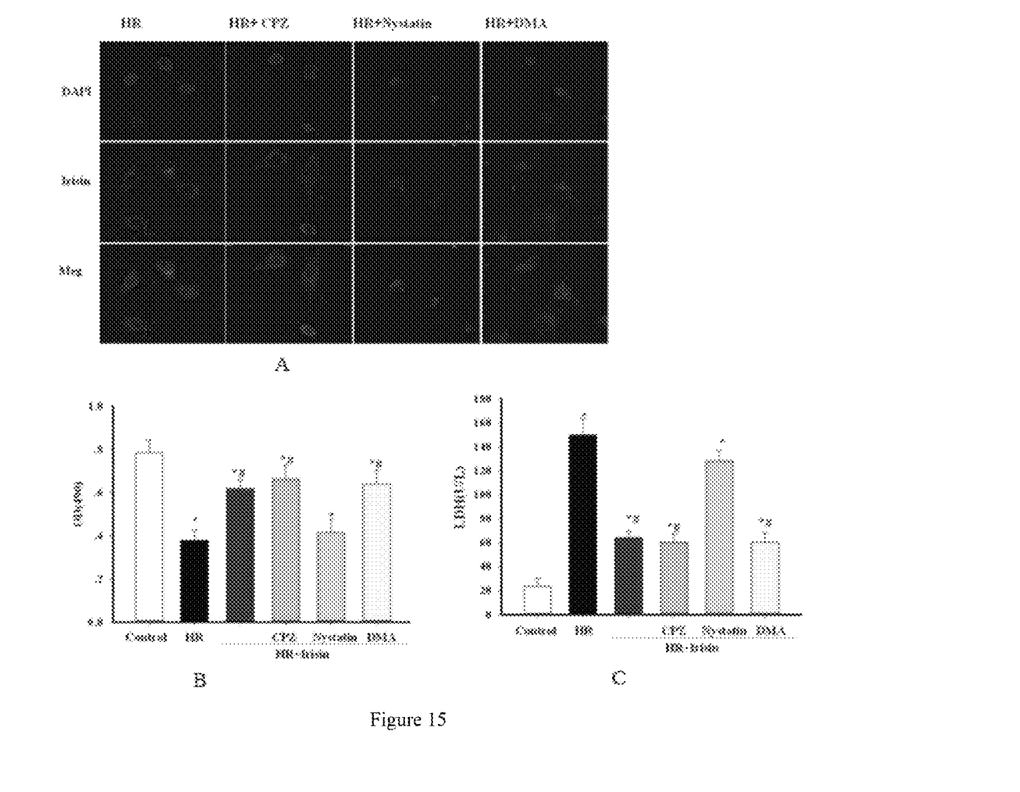
FIG. 15: A: immunofluorescence staining shows the irisin expression in H9C2 myocardial cells after hypoxia/reoxygenation with CPZ (an inhibitor of clathrin-mediated-endocytosis), Nystatin (an inhibitor of lipid raft-mediated-endocytosis), DMA (an inhibitor of macropinocytosis); B: cell viability; C: LDH concentration.

The HR+irisin group is further divided into four subgroups: group I is the HR+irisin group, group II is the HR+irisin+CPZ group (clathrin inhibitor), group III is the HR+irisin+Nystatin group (lipid raft inhibitor) and group IV is the HR+irisin+DMA group (giant endocytosis inhibitor). The localization of irisin on the hypoxia/reoxygenation injured H9C2 myocardial cells are determined by immunofluorescence (FIG. 15A). And the study also analyzes the LDH level (FIG. 15B) and the OD value of 490 nm wavelength (FIG. 15C). The results show that the OD value of the HR group is significantly reduced compared with that of the control group, the OD value level rises obviously after irisin treatment, no significant influence on the effect of inhibiting OD value lowering of irisin is produced after the CPZ and the DMA are added, and the OD value lowering capability of irisin is almost completely disabled after the Nystatin is added. Similarly, the CPZ and DMA have no obvious inhibiting effect on LDH concentration caused by the hypoxia/reoxygenation of irisin while the Nystatin inhibits the effect of irisin to a great degree in the LDH concentration level determination results. The results of the influence of irisin on the myocardial cells subjected to the $H_2O_2$ treatment are similar to the hypoxia/reoxygenation results. The two parts of the results indicate that the effect of resisting hypoxia/reoxygenation injuries of irisin is mediated by the lipid rafts in part.

Figure 16:
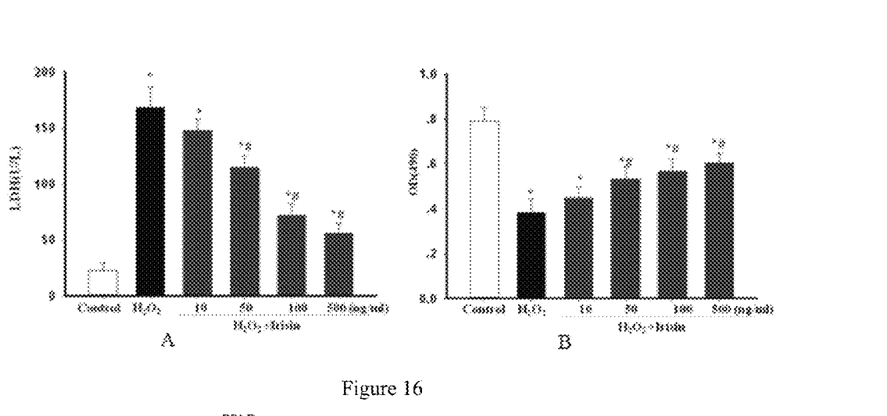
FIG. 16 shows the effect of irisin on the H9C2 myocardial cells after $H_2O_2$ treatment (A: LDH concentration; B: cell viability)

The H9C2 myocardial cells are cultured by above-mentioned method and then are divided into three groups: group I is the control group and does not need any treatment, group II is the H2O2 group (H2O2 is added into the H9C2 myocardial cells to reach the final concentration of 100 μM and then are cultured with 5% CO2 at 37° C. for 24 hours), group III is the H2O2+irisin group (irisin is added into the H9C2 myocardial cells, H2O2 is added after 30 minutes until the final concentration is 100 μM, and then the H9C2 myocardial cells are cultured in the 5% CO2 cell culture box at the temperature of 37° C. for 24 hours), the model box is put in the anoxic environment of 37° C. to perform oxygen deficiency for 16 hours and reoxygenation for 3 hours so as to form a hypoxia-reoxygenation model, then the LDH content is determined by utilizing the kit, optical density value detection is conducted at the position of 490 nm wavelength, and the results are shown in FIG. 16. As shown in FIG. 16, the results of the influence of irisin on the myocardial cells subjected to the H2O2 treatment are similar to the hypoxia/reoxygenation results. Irisin has the obvious capability of resisting hypoxia/reoxygenation injuries on the two aspects of OD value and LDH concentration.

IV. Irisin preventing I/R induced inflammation and oxidative stress is associated with PPARγ nuclear translocation promotion and NF-κB nuclear translocation inhibition.

Figure 17:
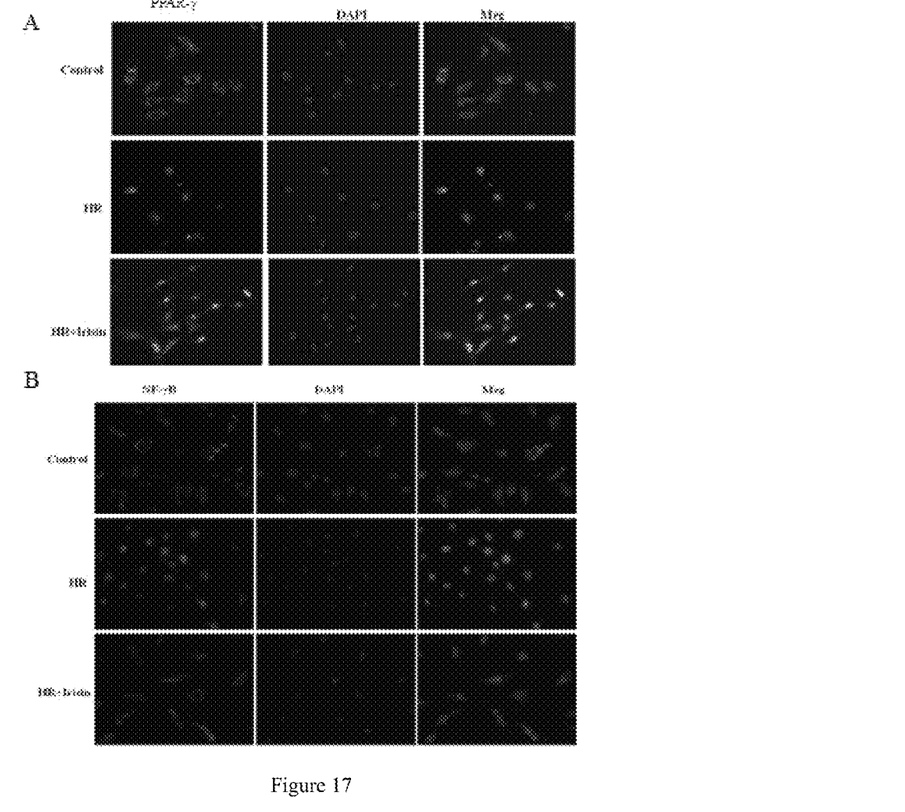
FIG. 17 shows the PPARγ (A) and NF-κB (B) nuclear translocation with irisin by immunofluorescence staining.

Immunofluorescence staining of H9C2 myocardial cells in the control group, the HR group, and the HR+irisin group. Cells are fixed and permeabilized with 100% methanol (30 min). After washing with PBS three times and treating with 0.3% methyl alcohol, cells, grown on coverslips, are blocked with 5% goat serum in PBS at room temperature for 1 hour, and incubated with PPAR-γ primary antibody (1:50) at 4° C. overnight, followed by TRITC-goat anti-rabbit IgG antibody (goat anti-rabbit), performing incubation at the temperature of 37° C. for 40 minutes at 37° C. for 40 minutes. After staining with DAPI, the slides were permanently mounted for acquiring image by fluorescent microscope. The results are shown in FIG. 17. As shown in FIG. 17, the PPAR-γ in the control group is mainly located in the cytoplasm, the NF-κB content of the endochylema is higher, and the NF-κB content of the nuclei is lower; the PPAR-γ in the HR group is expressed both in the endochylema and the nuclei, the IκB content of the endochylema is greatly reduced, and the NF-κB content of the nuclei is increased; the PPAR-γ in the HR+irisin group (compared with the HR group) is mainly distributed in the nuclei, endochylema caveolin 1 and NF-κB expressions are increased, and the NF-κB content of the nuclei is lowered.

Figure 18:
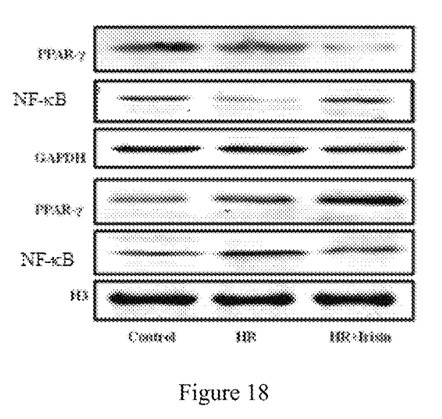
FIG. 18 shows the PPARγ and NF-κB nuclear translocation with irisin by immunoblotting.

Meanwhile, PPARγ and NF-κB expressions in the cytoplasms and the nuclei in the control group, the HR group, and the HR+irisin group, determined by immunoblotting, are shown in FIG. 18. Under normal circumstances, the PPAR-γ is mainly distributed in the cytoplasms, when hypoxia-reoxygenation occurs, and the PPAR-γ cannot be effectively translocated to the nuclei to inhibit the NF-κB activity due to a caveolin 1 expression drop. Under normal circumstances, the NF-κB is combined with the PPAR-γ into a complex in the endochylema, the NF-κB content drops because of hypoxia-reoxygenation, and accordingly the NF-κB translocated towards the nuclei is increased. It is indicated that irisin increases caveolin 1 expressions so as to promote PPAR-γ translocation towards the nuclei, the PPAR-γ is combined with the NF-κB in the nuclei to inhibit the transcription activity of the inflammatory factors related to target genes; in addition, irisin enables the IκB content to rise, and accordingly the NF-κB translocated towards the nuclei is decreased.

Finally, the above preferred embodiments are only illustrative for the technical scheme of the invention and are not limiting. Although the preferred embodiments have been already described in detail for the invention, it should be appreciated that skilled persons in the prior art can make a variety of changes in form and detail without departing from the scope defined by the claims of the invention.

What is claimed is:

1. A method, comprising:
    administering an amount of irisin either before or after a heart ischemia reperfusion of a rat for reducing myocardial ischemia reperfusion damages, wherein the amino acid sequence of the irisin is SEQ ID NO:1.

2. The method according to claim 1, wherein: the administering of the irisin reduces myocardial infarction caused by the myocardial ischemia reperfusion, compared with administering of one or more of an antibody pre-adsorbed irisin and a heat-inactivated irisin.

3. The method according to claim 1, wherein: the administering of the irisin reduces a myocardial enzyme marker rise caused by the myocardial ischemia reperfusion, compared with administering of one or more of an antibody pre-adsorbed irisin and a heat-inactivated irisin.

4. The method according to claim 3, wherein the myocardial enzyme marker is lactic dehydrogenase, troponin or creatine kinase.

5. The method according to claim 1, wherein: the administering of the irisin reduces a inflammatory response caused by the myocardial ischemia reperfusion, compared with administering of one or more of an antibody pre-adsorbed irisin and a heat-inactivated irisin.

6. The method according to claim 1, wherein: the administering of the irisin reduces an oxidative stress caused by the myocardial ischemia reperfusion, compared with administering of one or more of an antibody pre-adsorbed irisin and a heat-inactivated irisin.

7. The method according to claim 1, wherein: the administering of the irisin reduces a myocardial apoptosis caused by the myocardial ischemia reperfusion, compared with administering of one or more of an antibody pre-adsorbed irisin and a heat-inactivated irisin.

8. The method according to claim 1, wherein: the administering of the irisin promotes a peroxysome proliferator-activated receptor γ nuclear translocation, compared with administering of one or more of an antibody pre-adsorbed irisin and a heat-inactivated irisin.

9. The method according to claim 1, wherein: the administering of the irisin inhibits a nuclear transcription factor NF-κB nuclear translocation, compared with administering of one or more of an antibody pre-adsorbed irisin and a heat-inactivated irisin.

10. The method according to claim 1, further comprising: administering the irisin 30 minutes before the heart ischemia reperfusion.

11. The method according to claim 1, further comprising: administering the irisin immediately after the heart ischemia reperfusion.

12. The method according to claim 1, wherein the amount of the irisin ranges from 0.1 μg/kg to 5 μg/kg.

13. The method according to claim 1, wherein the amount of the irisin is 5 μg/kg.

\* \* \* \* \*

SEQUENCE LISTING

```
<160> NUMBER OF SEQ ID NOS: 1

<210> SEQ ID NO 1
<211> LENGTH: 113
<212> TYPE: PRT
<213> ORGANISM: Artificial Sequence
<220> FEATURE:
<223> OTHER INFORMATION: Irisin amino acid sequences

<400> SEQUENCE: 1

Asp Ser Pro Ser Ala Pro Val Asn Val Thr Val Thr Val Arg His Leu
1               5                   10                  15

Lys Ala Asn Ser Ala Val Val Ser Trp Asp Val Leu Glu Asp Glu Val
            20                  25                  30

Val Ile Gly Phe Ala Ile Ser Gln Gln Lys Lys Asp Val Arg Met Leu
        35                  40                  45
```

-continued

```
Arg Phe Ile Gln Glu Val Asn Thr Thr Arg Ser Cys Ala Leu Trp Asp
    50                  55                  60

Leu Glu Glu Asp Thr Glu Tyr Ile Val His Val Glu Ala Ile Ser Ile
65                  70                  75                  80

Gln Gly Glu Ser Pro Ala Ser Glu Pro Val Leu Phe Lys Thr Pro Arg
                85                  90                  95

Glu Ala Glu Lys Met Ala Ser Lys Asn Lys Asp Glu Val Thr Met Lys
            100                 105                 110

Glu
```